United States Patent [19]

Kallet

[11] 4,345,837
[45] Aug. 24, 1982

[54] ENHANCED FLUORESCENT EMISSION
[75] Inventor: Eli A. Kallet, New York, N.Y.
[73] Assignee: Farrand Optical Co., Inc., Valhalla, N.Y.
[21] Appl. No.: 163,846
[22] Filed: Jun. 27, 1980
[51] Int. Cl.³ ............................................. G01N 21/64
[52] U.S. Cl. ................................. 356/317; 356/244; 356/301
[58] Field of Search ................ 356/317, 318, 301, 244

[56] References Cited

U.S. PATENT DOCUMENTS 3,414,354 12/1968 Siegler, Jr. ..................... 356/301
3,704,951 12/1972 Chupp ........................... 356/318 X
3,825,325 7/1974 Hartley et al. ................. 356/301 X
4,088,407 5/1978 Schoeffel et al. ............... 356/317 X

*Primary Examiner*—Vincent P. McGraw
*Attorney, Agent, or Firm*—John L. Downing

[57] ABSTRACT

Monochromatic exciting light is transmitted in a forward direction from a source through a sample to a spherical mirror. The spherical mirror reflects the light in a backward direction through the sample and images the light upon a flat mirror. The flat mirror reflects the light in the forward direction, through the sample, to the spherical mirror, thereby causing the light to be reflected in the backward direction, through the sample, to the source. The reflections increase the optical path length of the light through the sample, thereby enhancing a fluorescent emission therefrom.

4 Claims, 1 Drawing Figure

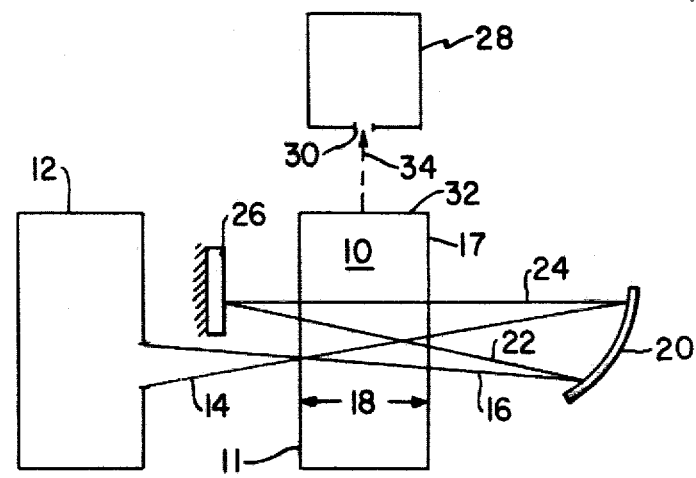

ENHANCED FLUORESCENT EMISSION

BACKGROUND OF THE INVENTION

1. Field of the Invention

This invention relates to optics, and more particularly to obtaining an increased fluorescent emission from a sample that is being analyzed.

2. Description of the Prior Art

In one type of analysis, fluorescent emission of light is obtained from a sample of a component if a fluid in response to a transmission thereto of monochromatic light. The spectral content of the emission is determined by the composition of the component. Because the emission is determined by the composition, emission from components comprising the fluid are often collectively referred to as a signature of the fluid.

To obtain the sample, the components comprising the fluid are, for example, chromotographically separated by forcing the fluid through an absorbing column. The column is typically comprised of silica gel particles. Each of the components pass through the column at a unique velocity, thereby causing the components to pass a known location in the column with a temporal separation therebetween. An exit line from the column usually feeds a thin walled cell of an instrument for measuring light, whereby the sample is within the cell at a known time. It should be appreciated that the sample is usually small.

An exciting beam of light is transmitted through the cell to cause the fluorescent emission. The intensity of the emission radiation is in a direct relationship with the path length of the exciting beam within the sample. However, since the sample is small, the path length is short.

It should be understood that the radiation emission is radial from the cell. Because the emission is radial, the light measuring instrument may be positioned to receive light emitted along a path angularly related to the path of the exciting beam. The light measuring instrument thereby receives a portion of the emission without receiving the exciting beam. Preferably, the path of the portion of the emission and the path of the exciting beam are perpendicular to each other.

For reasons given hereinbefore, it is desirable to have apparatus that provides an increased path length of the exciting beam within the sample. Moreover, it is desirable that the angular relationship, referred to hereinbefore, be retained.

SUMMARY OF THE INVENTION

According to the present invention, light is transmitted in a forward direction from a source through a sample to a first reflector to form a first reflected beam of light that is reflected in a backward direction through said sample to a second reflector, said forward and backward directions having an angular relationship to the path of a fluorescent emission of light from said sample; in response to said first beam, said second reflector reflects a second beam of light in said forward direction through said sample to said first reflector, thereby causing a third beam of light to be reflected in said backward direction through said sample.

The invention provides a simple apparatus for enhancing fluorescent emission from a sample by providing at least four paths of exciting light through the sample.

Other features and advantages of the present invention will become more apparent in the light of the following detailed description of a preferred embodiment thereof as illustrated in the accompanying drawing.

BRIEF DESCRIPTION OF THE DRAWING

The sole FIGURE herein is a schematic block diagram of the preferred embodiment of the present invention.

DESCRIPTION OF THE PREFERRED EMBODIMENT

The present invention is predicated upon the well known principle of reversibility in optics. According to the principle, an object imaged at an original position by an optical system will if placed in the image plane at the imaged position be imaged at the original object position.

As shown in the drawing, a sample is within a thin walled cell 10 of the type used in chromotographic separation. The cell 10 has the general shape of a rectangular parallelpiped and is disposed with a proximal wall 11 thereof in the image plane of a monochromator 12.

The monochromator 12 transmits an exciting beam of light in a forward direction. The exciting beam is imaged upon or near the transparent wall 11. The path of the exciting beam is exemplified by rays 14, 16.

The exciting beam passes through the cell 10 (and the sample) and emerges from the distal wall 17 of the cell 10, the walls 11, 17 being opposite each other. The exciting beam causes a radial fluorescent emission of light from the sample. It should be understood that the strength of the emission is substantially in a direct relationship with a length 18 of the path of the exciting beam through the sample. As explained hereinafter, light comprising the exciting beam is reflected to provide a path length through the sample that is four times the path length 18.

The cell 10 is disposed with the wall 17 opposite a focussing spherical mirror 20. The mirror 20 reflects the emerging exciting beam in a backward direction, thereby causing the light comprising the exciting beam to form a first reflected beam of light having a path exemplified by rays 22, 24. The mirror 20 is tilted to cause an angular displacement between the central axes (not shown) of the exciting beam and the first beam.

The first beam passes through the wall 17 and emerges from the wall 11. Because the mirror 20 is tilted, the first beam is imaged upon a flat mirror 26 that has a reflecting surface at the image plane opposite the wall 17. Therefore, the first beam has the path length 18 through the cell 10. Since the image is formed at the reflecting surface of mirror 26, this image acts as a new source of excitation.

The mirror 26 reflects the first beam substantially in the forward direction thereby causing the light comprising the first beam to form a second reflected beam of light. In this embodiment, the mirror 26 causes the second beam to pass through the wall 11 and emerge from the wall 17, whereby the second reflected beam has the path length 18 through the cell 10. Moreover, the mirror 26 causes the second beam to be transmitted along the path exemplified by the rays 22, 24. Therefore, the second beam is transmitted to the mirror 20. Hence, the mirror 26 acts as a source of light that is transmitted to the mirror 20 along the path of light (the first beam) reflected therefrom.

In accordance with the principle of reversibility, the mirror 20 causes the light comprising the second beam to form a third reflected beam of light that passes through the cell 10 to the monochromator 12 along the path exemplified by the rays 14, 16. Hence, the third beam has the path length 18 through the cell 10.

Since the three reflected beams and the exciting beam have the path length 18 through the cell 10, the light comprising the exciting beam is reflected to provide the path length through the sample that is four times the path length 18, thereby causing the sample 10 to provide an enhanced fluorescent emission.

In this embodiment, a monochromator 28 has an input slit 30 that receives a portion of the enhanced emission which emerges from a wall 32 of the cell 10. Since the cell 10 has the shape of a rectangular parallelpiped, the wall 32 is perpendicular to the walls 11, 17. Moreover, the portion of the enhanced emission is exemplified by rays 34 and has a path that is substantially in a perpendicular relationship with the paths of the exciting and the reflected beams. It should be understood that the perpendicular relationship prevents lights from the exciting and reflected beams from passing through the slit 30.

In an alternative embodiment, either an elliptical mirror (or a combination mirror—refractor) is used in place of one mirror 20 to provide an increased focal length, whereby light is reflected from the mirror 26 and imaged upon an additional flat mirror near the wall 17. In accordance with the principle of reversibility, the additional flat mirror reflects light to the monochromator 12 via reflections from the mirror 26 and the elliptical mirror. Accordingly, the alternative embodiment provides a path length through the sample that is approximately six times the path length 18. In a similar manner, an even greater path length through the sample may be provided.

Although the preferred embodiment is related to enhancing fluorescent emission, it should be understood that the invention may be used whenever it is desired to provide an increased path length of light.

What is claimed is:

1. In a method of providing an increased path length of light through a sample wherein a light source transmits an exciting beam of light through said sample in a forward direction, the improvement comprising the steps of:

reflecting said exciting beam from a first reflector in a backward direction along a known path through said sample, thereby forming a first reflected beam; and imaging said first reflected beam upon the surface of a second reflector to cause a second reflected beam to be reflected in said forward direction along said known path through said sample to said first reflector and to be reflected directly back to said light source.

2. Apparatus for providing an increased path length of light through a sample cell wherein an exciting beam of light from a light source is transmitted in a forward direction toward a proximal wall of said cell and emerges from a distal wall, the improvement comprising:

first reflector means responsive to said emerging exciting beam for forming a first reflected beam that is transmitted through said cell in a backward direction along a known path and imaged at a surface adjacent the proximal wall of said cell; and second reflector means positioned at said surface for forming a second reflected beam directed in a forward direction along said known path through said sample to said first reflector, whereby the exciting beam is reflected directly back to said light source.

3. Apparatus according to claim 2 wherein said first reflector is a spherical mirror.

4. Apparatus according to claim 2 wherein said second reflector is a plane mirror.

* * * * *